US008722394B2

(12) United States Patent
Tasch et al.

(10) Patent No.: US 8,722,394 B2
(45) Date of Patent: May 13, 2014

(54) LABORATORY APPARATUS WITH AN ARRANGEMENT FOR THE TEMPERING OF SAMPLES AND METHOD OF TEMPERING SAMPLES

(76) Inventors: Henner Tasch, Hamburg (DE); Andreas Schirr, Hamburg (DE); Lutz Timmann, Fuhlendorf (DE)

( * ) Notice: Subject to any disclaimer, the term of this patent is extended or adjusted under 35 U.S.C. 154(b) by 465 days.

(21) Appl. No.: 12/972,093

(22) Filed: Dec. 17, 2010

(65) Prior Publication Data

US 2011/0151519 A1 Jun. 23, 2011

Related U.S. Application Data

(60) Provisional application No. 61/289,701, filed on Dec. 23, 2009.

(30) Foreign Application Priority Data

Dec. 23, 2009 (EP) .................................... 09015976

(51) Int. Cl.
*C12P 19/34* (2006.01)
*C12M 1/00* (2006.01)

(52) U.S. Cl.
USPC ..................... 435/287.2; 435/289.1; 435/91.2

(58) Field of Classification Search
USPC .................................. 435/287.2, 289.1, 91.2
See application file for complete search history.

(56) References Cited

U.S. PATENT DOCUMENTS

| | | | | |
|---|---|---|---|---|
| 6,703,236 | B2 | 3/2004 | Atwood | |
| 7,051,536 | B1 | 5/2006 | Cohen et al. | |
| 2007/0230535 | A1* | 10/2007 | Atwood et al. .................. | 374/1 |

FOREIGN PATENT DOCUMENTS

| | | | |
|---|---|---|---|
| EP | 1 710 017 | A1 | 10/2006 |
| WO | WO 98/20975 | A1 | 5/1998 |
| WO | WO 01/08800 | A1 | 2/2001 |
| WO | WO 2004/018105 | A1 | 3/2004 |
| WO | WO 2009/034988 | A1 | 3/2009 |
| WO | WO 2010/012494 | | 2/2010 |

OTHER PUBLICATIONS

Extended European Search Report, European Patent Office, regarding European Patent Application No. 09015976, held in the name of Eppendorf AG, mailed Apr. 13, 2010.

* cited by examiner

*Primary Examiner* — William H Beisner
*Assistant Examiner* — Danielle Henkel
(74) *Attorney, Agent, or Firm* — Todd Lorenz; Arnold & Porter LLP

(57) ABSTRACT

The invention relates to a laboratory apparatus, in particular for performing a polymerase chain reaction (PCR) in a plurality of PCR-samples, which comprises an arrangement for tempering samples, the arrangement comprising a tempering block for the tempering of samples, the tempering block comprising a reception side, which provides receptacles for receiving sample vessels, and a contact side for the contact of at least one tempering device, at least one tempering device, arranged in an area of said contact side, a pressure device, which comprises a pressure element and an auxiliary element, said at least one tempering device being arranged between said auxiliary element and the tempering block, the pressure element being linked to said auxiliary element and to the tempering block, and being arranged to press said at least one tempering device against the tempering block by pressing said auxiliary element against said at least one tempering device, wherein at least one tempering device is shaped and arranged in said area to at least partially surround by itself said pressure element.

16 Claims, 11 Drawing Sheets

Figure 1:
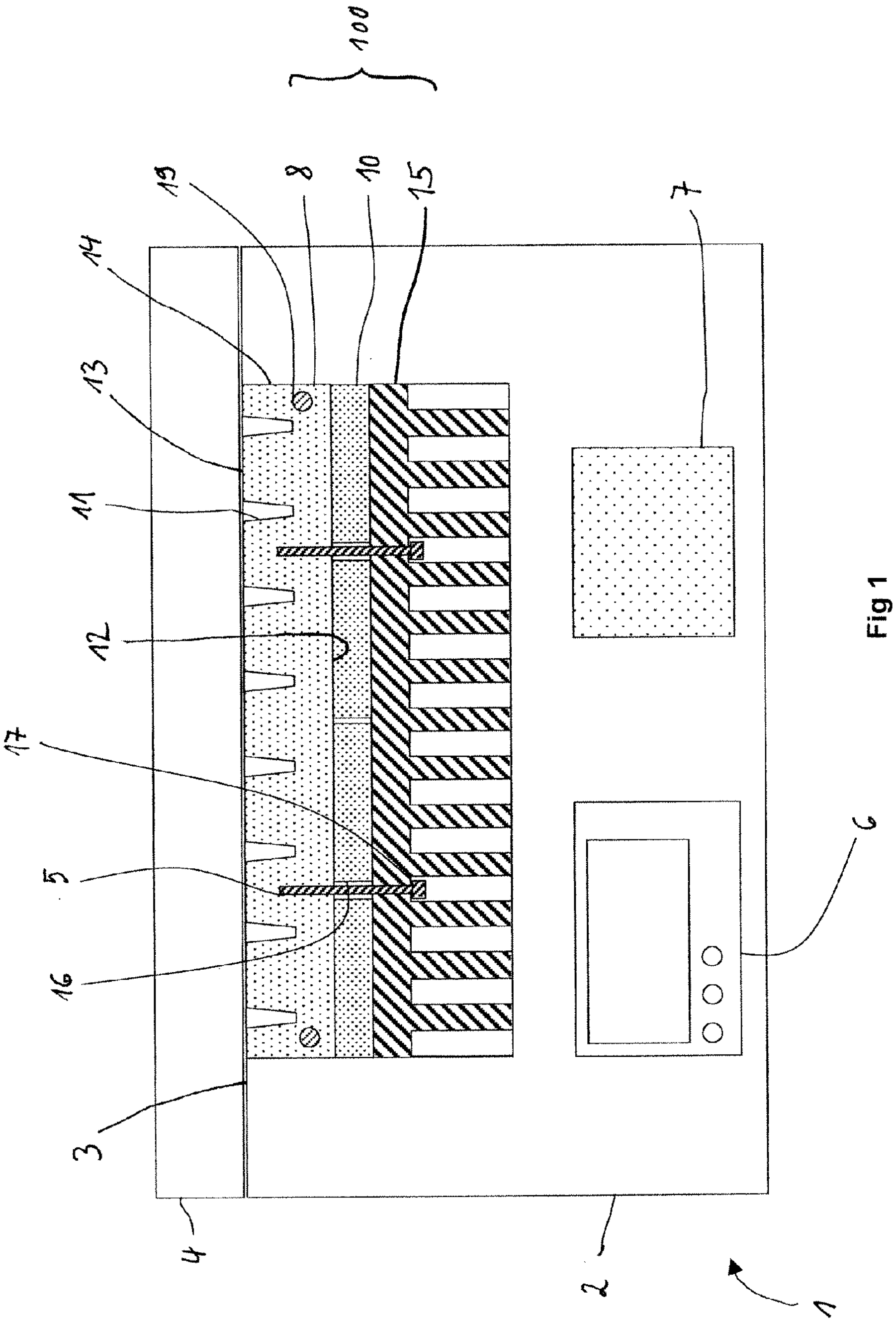

LABORATORY APPARATUS WITH AN ARRANGEMENT FOR THE TEMPERING OF SAMPLES AND METHOD OF TEMPERING SAMPLES

The invention relates to a laboratory apparatus with an arrangement for the tempering of samples and a method of tempering samples by means of an arrangement for tempering samples.

Such laboratory apparatus are being used for example as thermostats, thermomixers or thermocyclers in examination- or research laboratories for tempering a plurality of samples, for example for bringing liquid samples to a desired temperature. The precise adjustment of predetermined temperatures in samples is in particular important for chemical, biological or biochemical reactions, whose successful execution depends in a critical way on the compliance with at least one certain temperature or with a temporarily or spatially changing temperature profile. An example for such reaction is the polymerase chain reaction (PCR). By such a PCR reaction DNA-sequences can be efficiently amplified, for which reason said method is applied with increasing importance, for example in pharmacy, medicine, research or forensic science.

The precise adjustment of certain temperature values, to which a sample is cyclically subjected during a PCR tempering program, is critical for the successful performance of a PCR, in particular of a quantitative PCR. In a PCR, the cycle periods of denaturation, primer hybridization and elongation are controlled by different precisely defined temperature levels. Usually, a plurality of PCR-samples are exposed to the same target temperature by the laboratory apparatus, simultaneously.

For that purpose, a tempering device, for example a Peltier element, is placed below a tempering block, which contains the sample vessels with the PCR-samples, and the tempering device is used to temper the tempering block to a target temperature or through a temperature profile. This usually requires a temperature sensor positioned at the tempering block, which controls the actual temperature and allows to control the power, which drives the tempering device, by a closed-loop control. This way, the tempering block is controlled to reach and keep the value of the target temperature, at least at the position of the temperature sensor. However, the temperatures of the tempering block at those positions, which are not monitored by temperature sensors, are undetermined. In an ideal arrangement, which comprises the tempering block with the sample receptacles and the tempering device, the tempering block reaches a uniform temperature, at least within a section of the tempering block, which contains said samples, which have to be kept at the same temperature.

However, an ideal uniformity of a temperature block is hardly to achieve. Multiple inhomogeneities of the system, including the apparatus, the samples and the environment, can interfere. For example, the tempering block and the tempering device have edges, therefore a spatial inhomogeneity is inevitable. However, it is desirable to reduce the effect of such a spatial inhomogeneity. Moreover, the contact of the Peltier element to the tempering block is crucial, because an inhomogeneous contact surface will lead to an inhomogeneous transfer of heat to the tempering block, and therefore to a non-uniform temperature distribution over the tempering block. It is therefore important, to improve said contact by means of a pressure device, which presses the tempering device against the tempering block. This, in consequence, requires a preferably uniform pressure to be applied.

In known devices, for example in the device described by U.S. Pat. No. 7,051,536 B1, clamps are used for pressing the tempering device to the underside of a tempering block, wherein the tempering device is pressed against the tempering block by means of components, which are arranged below and aside from the tempering block, in particular by fasteners, which are positioned aside and which are the source of the pressure. Having the fasteners positioned aside by a distance from the tempering block creates a torque, which is proportional to the force and to the lever distance. The torque is acting on the components non-stop, starting from the moment of assembly. Such an arrangement therefore critically depends on the finite stiffness of the components, which distribute the pressure, which is generated outside from the tempering block, along the underside of the tempering device. The torque is tending to cause a non-uniformity of the pressure, which acts on the tempering device. Further, such an arrangement is particular sensible for material fatigue of said components over time, when a bending of said components occurs, which further degrades the pressure uniformity.

It is the object of the present invention to provide an improved laboratory apparatus with an improved arrangement for tempering samples, and to provide a method for tempering samples.

The object is met by the laboratory apparatus according to claim 1 and the method according to claim 16 of the present invention. Preferred embodiments of the invention are subjects of the sub-claims.

The laboratory apparatus according to the invention, in particular for performing a polymerase chain reaction (PCR) in a plurality of PCR-samples, comprises an arrangement for tempering samples, the arrangement comprising a tempering block for the tempering of samples, the tempering block comprising a reception side, which provides receptacles for receiving sample vessels, and a contact side for the contact of at least one tempering device, at least one tempering device, arranged in an area of said contact side, a pressure device, which comprises a pressure element and an auxiliary element, said at least one tempering device being arranged between said auxiliary element and the tempering block, the pressure element being linked to said auxiliary element and to the tempering block, and being arranged to press said at least one tempering device against the tempering block by pressing said auxiliary element against said at least one tempering device, wherein at least one tempering device is shaped and arranged to at least partially surround by itself said pressure element.

Such a laboratory apparatus preferably is a thermomixer for the simultaneous mixing and tempering of at least one or two samples, or is a thermostat, which preferably is configured for the execution of a tempering program of at least one or two samples. The tempering program thereby comprises at least the step of tempering at least one sample to a least one target temperature. This is preferably carried out by the manual or automatic setting of at least one set temperature as a target temperature at said at least one control loop.

Further, said tempering apparatus preferably comprises the function of a thermocycler or is configured as a thermocycler. The latter is preferably appropriate to carry out a PCR reaction within at least one PCR sample. Said tempering apparatus is preferably a thermocycler. The tempering program thereby preferably comprises at least the tempering steps of a PCR cycle during whom the PCR sample is tempered in a temporal sequence to at least two or three temperatures. By means of a single tempering program a PCR reaction within at least one PCR sample is preferably executed by repeating the tempering steps of a PCR cycle multiple times, in particular 10 to 70 times.

It can be desirable to find out the optimal temperature levels of a PCR by applying a spatial temperature gradient, i.e. a spatially changing temperature profile with at least two different temperatures. For said purpose, a temperature gradient is generated in the tempering block along a distance, along which also a plurality of PCR samples are arranged to, which therefore are exposed to different temperatures, which lead to PCR results of differing quality. The temperature gradient can, for example, be generated by at least two tempering devices, which are arranged below the tempering block, as it is described in the WO 98/020975 A1. This offers the advantage that the tempering block can also be brought to a uniform temperature by generating the same temperature by means of said at least two tempering devices. Moreover, a temperature gradient can be used to hold the samples, which are provided in the receptacles of a tempering block at different temperatures which is, for example, reasonable if the samples are group-wise running through different reaction phases. Thus, a temperature gradient can have continuous temperature changes or can be step-shaped. Alternatively, the generation of a temperature gradient can be provided by other arrangements, wherein at least two different temperatures are applied to the tempering block.

Other possible laboratory apparatus are work stations and other apparatus, which can apply a tempering program simultaneously to multiple samples.

The arrangement, the tempering block, the tempering device, the control device, and/or the control loops, respectively, is preferably based on the configurations according to the teachings described by WO 98/020975 A1 ("Gradienten-Temperierblock" by EPPENDORF AG) and/or PCT/EP2009/005583 ("Temperierungsvorrichtung mit Testmöglichkeit" by EPPENDORF AG).

A tempering block here refers to a component whose configuration allows to temper at least one sample, which is arranged at or in the tempering block. Preferably, the tempering block comprises at least one preferably integrally formed, preferably substantially cuboidal-shaped component, preferably made from a well heat-conducting material, in particular metal, for example aluminium or silver. Moreover, it is possible that said tempering block is divided into at least two, in particular three, four, five, six or more integrally formed sections made from a well heat-conducting material, which are separated by a worse heat-conducting medium or material. Within said component or within each of said sections, preferably at their upper surface, at least one receptacle for a sample or a sample vessel is arranged at a reception side of the tempering block. Whenever a tempering block is mentioned in the following, it also refers to a tempering block section, if not described otherwise or if not reasonable.

Said receptacle is preferably arranged as a recess at the surface of said section or said tempering block, which preferably provides further recesses to reduce the total block mass. Further, the tempering block preferably provides a base plate, preferably with a flat contacting side, with receptacles arranged integrally or soldered to said base plate on top, wherein the receptacles are preferably laterally connected by heat transferring connection bars, which are also connected in the similar way to the base plate. Such a configuration allows to configure the tempering block to provide a lower total mass, which can be heated and cooled faster than a block with a higher mass. Said receptacle or the recess are preferably configured for a large-area contacting of a sample vessel, which preferably means the depth of the receptacle has at least the dimension of preferably at least the maximum width of the receptacle, and which further preferably means that the roughness of the inner surface of the receptacle is at least as low as the roughness of standard PCR-vessels, e.g. PCR-vessels by EPPENDORF AG. Thereby, an efficient heat transfer from the tempering block to the sample vessel and to the sample volume contained therein can be achieved.

Preferably, said tempering block is configured for the reception of a plurality of samples or sample vessels. Preferably, said tempering block is configured for the reception of at least one sample plate, at which a number of sample vessels are arranged side by side. Such a sample plate is preferably a microtiter plate or a PCR plate. Preferably, such a sample plate is a "twin.tec PCR plate" by EPPENDORF AG. Preferably, said tempering block is configured for the reception of a number of single sample vessels, in particular 0.5 ml or 0.2 ml PCR vessels, in particular by EPPENDORF AG. Said number of sample vessels is, in particular, respectively preferred 2, 4, 8, 12, 16, 24, 48, 96, 384 or 1536.

The tempering device is preferably assigned to a control loop and is preferably an electrically controllable device. Preferably, said tempering device comprises a Peltier element. However, another type of tempering device can be provided, for example comprising an electrically resistive element. For the tempering of said at least one tempering block the tempering device is preferably arranged under the tempering block, at the contact side. The tempering device preferably contacts the tempering block in a large-area manner, wherein said tempering device provides a dimensioning, which allows the tempering of a plurality of samples by means of a single tempering device. To achieve this, the tempering device is preferably arranged at the contact side opposite to a plurality of receptacles for samples or sample vessels, which are arranged opposite to said tempering device in the tempering block at the reception side.

To each tempering device at least one temperature measurement device is assigned. Therefore, said temperature measurement device is appropriate to measure the temperature, which is adjusted to said tempering block by means of said tempering device. For the detection of the temperature of the tempering block said temperature measurement device is preferably arranged at said tempering block. A temperature measurement device is preferably attached to the tempering block, for example adhered to, or preferably at least in part incorporated into a recess or opening of the tempering block. The temperature measurement device is preferably an electronic component and can, for example, comprise a semiconductor temperature sensor, a thermoelement or a pyrometer.

Preferably a control device is provided, which preferably comprises electrical circuits, which are configured for the control of the tempering of the at least one tempering block. Further, said control device preferably comprises means for the digital data processing. The control loop preferably comprises a processing unit, which can be a CPU, a microprocessor or a microcontroller. Preferably, said control device comprises circuits, which are configured for processing a program code, in particular for the processing of programs for the temperature regulation. Further, the control device preferably comprises at least one memory unit for the storage of data or signals, which preferably is also removable from the control device. Said memory unit preferably comprises data storage for the temporary storage of data, for example RAM and/or data storage for the permanent storage of date, for example hard disc or flash memory. Further, said control device preferably comprises at least one interface for establishing a signal-connection between said control device and another device, for example a testing device in an external embodiment, to an external data storage, to a control apparatus, to an external PC, to a control panel or to another device. Further, said control device preferably comprises circuits, for example power electronics, for a control of components for the energy supply, which can serve, for example, for the power supply of said control device, said at least one tempering device or said at least one temperature measurement device. For the regulation of a temperature within said tempering block by means of said control loop, said control device is signal-connected to said at least one control loop and to at least one temperature measurement device, which is assigned to said at least one control loop.

The pressure device serves to press said at least one tempering device against the contact side of the tempering block. For that purpose, the pressure device comprises components, which are adapted to press said at least one tempering device against the contact side of the tempering block or comprises components, which are adapted to assist to press said at least one tempering device against the contact side of the tempering block or comprises components, which are adapted to improve the effect (or another related side effect) of pressing said at least one tempering device against the contact side of the tempering block.

The pressure element serves to press said at least one tempering device against the tempering block. The pressure element can be a single component or can comprise a fastener, like a screw, a clamp or any means, which is capable to generate or to maintain said pressure. Further, a component of the pressure element can be such means, which assist to generate or to maintain a pressure, or which assist any other function of the pressure element, for example, the pressure element serves to link the auxiliary element to the tempering block, in order to press said auxiliary element against said at least one tempering device. Therefore, any component which assist said linkage, is preferably assigned to said pressure element, like center sleeves, threads, bores, sealing means and the like.

Preferably, the pressure element comprises a cylindrical-shaped screw, e.g. an extension bolt, with a head. The latter preferably serves as a counter support, which takes up the pressure force, which arises if the head is pulled towards an optional opening of the auxiliary device, where it abuts, while an elastic extension of the screw generates the pressure upon screwing. A cylindrical coil or other spring means can be comprised by the pressure element. Such spring means is preferably arranged between the counter support of a pressure element and the auxiliary element. By means of the spring characteristics, which can provide at least in part a section with the linear proportionality between the displacement, e.g. under compression, the resulting pressure force can be adjusted. Therefore, such a spring means is useful in applying a defined pressure, e.g. by fastening a screw by means of a torque meter or by adjusting the displacement of the screw, because the pressure increases by a lower rate. Thus a more precise and reproducible adjustment of the pressure becomes possible.

The auxiliary element of the pressure device assists to press said at least one tempering device against the tempering block. Preferably, the auxiliary element acts as an extension of the counter support of the pressure element, preferred. Preferably the auxiliary element abuts on the at least one tempering device, if the pressure element pulls the preferred counter support towards the tempering block, the counter support abuts on the optional opening (or recess) of the auxiliary device and pulls the auxiliary device against the tempering block, in consequence. Generally, it is possible to press the tempering device against the tempering block without using an auxiliary device. In this case, preferably, the mechanical stability of the tempering device has to be appropriate to withstand the pressure, and the stiffness of the tempering device is high enough to avoid bending of the tempering device on pressurizing the same. Nevertheless, typical ceramics, used in many peltier elements are too fragile to be used without auxiliary element.

Preferably, the auxiliary element comprises a plate, which preferably is adapted to provide the stiffness of a solid metal block, preferably aluminium, steel, silver, which are used as the preferred base material for the fabrication of the auxiliary element. The plate is preferably configured to provide a surface, which within the arrangement matches to the surface of the tempering device, which is to be pressed against the tempering block, by form closure, preferably. Preferably the surface is even (plane). Further preferred, the auxiliary element is adapted to serve as a heat sink for the heat, which is generated by said at least one tempering device. Preferably, a heat sink is adapted to serve as auxiliary element. A heat sink is understood to be a component, which is adapted or optimized to take up heat and transfer it to another medium, e.g. to air or to other cooling media, e.g. liquids, which can circulate or stream along the heat sink, being in thermal contact with the heat sink. Thermal contact means a contact, which allows the transport of heat from a warm first medium to a less warm second medium, which contacts said first medium. Preferably a heat sink is made from a well heat conducting material, e.g. a metal, as for example aluminium or silver or steel. The heat sink further comprises means to increase the surface of the heat sink, which is capable to transfer heat to the environment, to improve the cooling capability, wherein fins, openings, spirals etc. are possible means.

The at least one tempering device is shaped to at least partially surround by itself said pressure element. For example, a Peltier element is provided, which surrounds the thread of a screw. The tempering device surrounds the pressure element by itself, which means that one single tempering device is adapted to at least partially surround said pressure element. Preferably, said at least one tempering device is shaped and/or arranged to either preferably partially or preferably completely surround the pressure element. To completely surround means, that the pressure element is encompassed by a ring-section of the tempering device or respectively, that at least a portion of the pressure element is completely surrounded, e.g. the cylindrical portion of the cylindrical part of a screw. It does not necessarily require that the pressure element is surrounded by the tempering device in a way that it serves as a hull. To “surround” the pressure element partially by a (single) tempering device preferably means that the pressure element is arranged in the enveloping area of said tempering device.

Said area of the contacting side, in particular said enveloping area of a tempering device, preferably is the area, which is enveloped by a virtual line, which runs in the plane of a plane contact side, and which envelopes one, two or more contact surfaces, wherein a contact surface is the surface of a tempering device, which substantially contacts the tempering block on the contacting side. This means said area also includes the area between tempering devices, if applicable. Using another preferred definition, said area can be the area, which is enveloped by a virtual line which runs in the plane of an even contact side, and which envelopes the vertical projection of the silhouette of one, two or more tempering devices onto the contact side.

Having at least one tempering devices shaped and arranged in said area of the contacting side, where the tempering device contacts the tempering block, to at least partially surround the pressure element, which also preferably is arranged in said area, offers a much higher flexibility to configure said arrangement, which comprises the tempering block, the at least one tempering device and the pressure device. In particular, the advantage is provided to optimize the arrangement with regard to the uniformity of the distribution of pressure. Pressure elements can be arranged at the contact side without being limited by a fixed shape of the tempering devices, which otherwise would block large areas of the contact side and render them inaccessible for the pressure elements.

On the other hand, more freedom is gained for arranging one or more tempering devices at the contact side, because the position of a tempering device does not have to be adapted to the position of a pressure element, which usually limits the number of possible positions for the arrangement, but can be shaped and arranged to surround the pressure elements.

Preferably, a pressure element and at least one tempering device are arranged such that the pressure element crosses the geometrical center point of said tempering device. This way, the pressure applied by the pressure element preferably origins substantially in said center point. In consequence, the pressure can be more evenly distributed over the tempering device by the auxiliary element, e.g. a pressure plate, which results in a more even and long-term stable heat transfer from the tempering device to the tempering device and also to the auxiliary device, which can be a heat sink.

Preferably, a plurality of pressure elements is provided, which are respectively at least partially or completely surrounded by a single tempering device. This way, the pressure can be distributed more uniform or, respectively, an increased overall pressure can be applied e.g. to further improve the thermal contact. Preferably, at least two pressure elements are arranged in the same distance to the geometrical center point of said tempering device. Thus, the pressure distribution becomes more uniform by such a symmetrical distribution of the pressure elements around said center point.

Preferably, a tempering device is shaped to at least partially surround said pressure element by providing a tempering device, which comprises at least one opening. Said opening is preferably adapted to let at least one pressure element engage through said opening. Said opening can also be a cylindrical recess, which is preferably formed in a side wall of the tempering device, wherein said recess is preferably adapted to surround a pressure element at least partially.

Preferably, said tempering device is a flat component, which means that its height h is lower than its width w and its depth d, respectively. Preferably, h is smaller than (or equals) w and d, respectively, multiplied by a factor c, which can be taken from the group of factors {1, 0.5, 0.4, 0.25, 0.2, 0.1, 0.05, 0.01, 0.005, 0.001}. The value for w, d and h is preferably constant, respectively, at (substantially) each position of the tempering device, or is varying. Preferably, a tempering device is a substantially cuboidal-shaped or comprises a section, which is cuboidal-shaped. Preferably, the tempering device features a number of side walls, which can be such walls, which are perpendicular to a plane contact side of the tempering block. A side wall is preferably even, but can also be curved. Said number of side walls is most preferred 5, wherein preferably four side walls are cuboidal even and one preferably is configured curved. Other preferred numbers of side walls, as for example defined from edge to edge, are 2, 3, 4, 6, 7, 8, 9, 10, 11, 12 or more.

Preferably, at least two tempering devices are provided, are arranged side by side in an area of said contact side. Preferably, at least two tempering devices and a pressure element are respectively configured and arranged such that a distance d2, preferably a minimal distance d2, of said at least two tempering devices is provided. This offers the advantage, that a larger fraction of the contact side of the tempering block can be contacted, which can make the heat transfer more uniform. Preferably, d2 is smaller than the width or depth of said pressure element. Preferably, d2 is smaller than the diameter of said pressure element at a position of said pressure element, which has a minimal distance from said at least one tempering device. Preferably, d2 is smaller than (or equals) 'w' or 'd' or 'h', multiplied by a factor c, respectively, taken from the group of factors {10; 5; 2; 1; 0.5; 0.1; 0.05; 0.01; 0}. Preferably, d2 is taken from one of the ranges 0 to 10 mm; 0 to 5 mm; 0.5 to 5 mm; 1 to 5 mm; 1 to 4 mm; 1 to 3 mm; 1 to 2 mm.

Preferably, all tempering devices are arranged such that the distance between vicinal tempering devices is uniform at (preferably substantially) all positions. This improves the uniformity of the heat transfer over the tempering block. Preferably the geometrical arrangement between a tempering device and a number of receptacles is such that they are arranged in opposite, preferably in a way that each vertical tangent of a tempering device, vertical with respect to an horizontal even contact side, if (or as far as) applicable, does not cross the inner volume of a receptacle. This increases the uniformity of the heat transfer to the receptacles and the samples. Said number is, respectively preferred, 1, 2, 4, 6, 8, 10, 12, 16, 24, 32, 48, 96 or an number larger than one and smaller than (or equal to) the overall number of receptacles in the tempering block.

Preferably, a pressure element is arranged symmetrical in relation to a number of receptacles of the tempering block, which number preferably is 2, 3, 6 or more preferably 4. Preferably, a pressure element is arranged in the same distance to each receptacle of said number of receptacles of the tempering block, respectively.

The object underlying the invention is further solved by the method according to the invention for tempering samples by an arrangement, in particular in a laboratory apparatus. Using the description and definitions of the laboratory apparatus according to the invention, the method according to the invention is a method for tempering samples by means of a laboratory apparatus, in particular according to one of the previous claims, Laboratory apparatus, in particular for performing a polymerase chain reaction (PCR) in a plurality of PCR-sample, which comprises an arrangement for tempering, the arrangement comprising a tempering block for the tempering of samples, the tempering block comprising a reception side, which provides receptacles for receiving sample vessels, and a contact side for the contact of tempering devices, at least one tempering device, arranged at an area of said contact side, a pressure device, which comprises a pressure element and an auxiliary element, said at least one tempering device being arranged between said auxiliary element and the tempering block, the pressure element being linked to said auxiliary element and to the tempering block, and being arranged to press said at least one tempering device against the tempering block by pressing said auxiliary element against said at least one tempering device, wherein tempering is performed by means of at least one tempering device, which is shaped and arranged to at least partially surround by itself said pressure element.

The method can, in particular, be performed by an arrangement for tempering samples according to the invention, in particular in an laboratory apparatus according to the invention, which can be configured as thermomixer, thermostat or thermocycler, in particular for performing PCR.

Further according to the invention, using the description and definitions made for the laboratory apparatus according to the present invention, an arrangement for tempering samples, in particular in a laboratory apparatus, is provided, comprises a tempering block for the tempering of samples, the tempering block comprising a reception side, which provides receptacles for receiving sample vessels, and a contact side for the contact of at least one tempering device, at least one tempering device, arranged in an area of said contact side, a pressure device, which comprises a pressure element and an auxiliary element, said at least one tempering device being arranged between said auxiliary element and the tempering block, the pressure element being linked to said auxiliary element and to the tempering block, and being arranged to press said at least one tempering device against the tempering block by pressing said auxiliary element against said at least one tempering device, wherein at least one tempering device is shaped and arranged to at least partially surround by itself said pressure element.

Further features and advantages of the invention can be derived from the subsequent description of the figures and the drawings. Same reference signs in the figures substantially characterize the same components or method steps, to avoid repetitions.

FIG. 1 shows a mixed side- and cross sectional view of a laboratory apparatus according to an embodiment of the present invention.

Figure 2A:
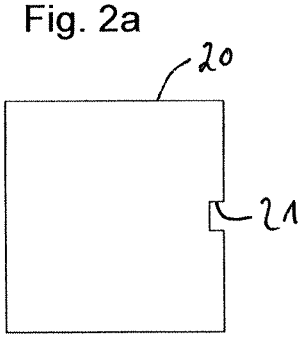

FIG. 2*a* shows the top view on a tempering device, or, respectively, the silhouette of the same in the top view, which is shaped to at least partially surround by itself the pressure element, for being arranged in a laboratory apparatus according to an embodiment of the present invention.

Figure 2B:
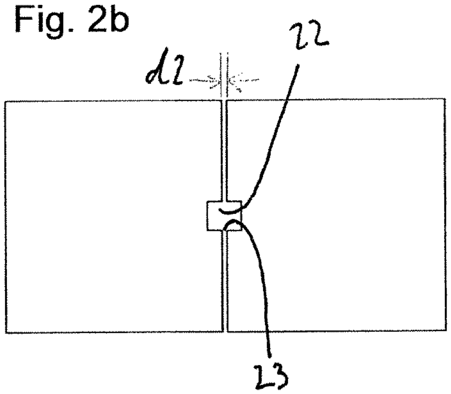

FIG. 2*b* shows the top view on two tempering device, arranged side by side, for being arranged in a laboratory apparatus according to an embodiment of the present invention.

Figure 3A:
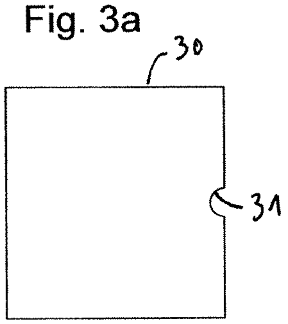

FIG. 3*a* shows the top view on another tempering device, which is shaped to at least partially surround by itself the pressure element, for being arranged in a laboratory apparatus according to another embodiment of the present invention.

Figure 3B:
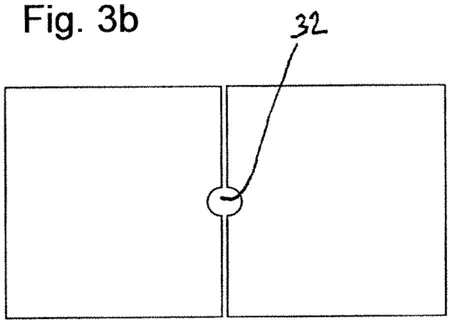
Figure 3C:
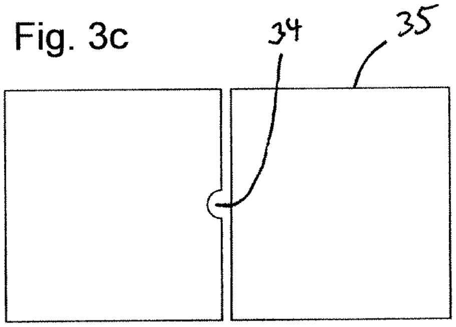

FIGS. 3*b* and 3*c* show the top view on two tempering devices, arranged side by side, for being arranged in a laboratory apparatus according to other embodiments of the present invention.

Figure 4A:
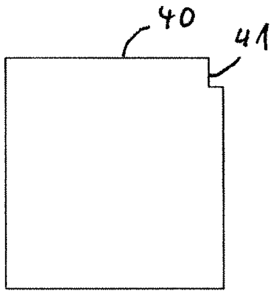

FIG. 4*a* shows the top view on another tempering device, which is shaped to at least partially surround by itself the pressure element, for being arranged in a laboratory apparatus according to another embodiment of the present invention.

Figure 4B:
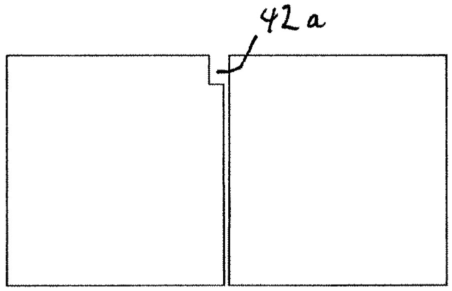
Figure 4C:
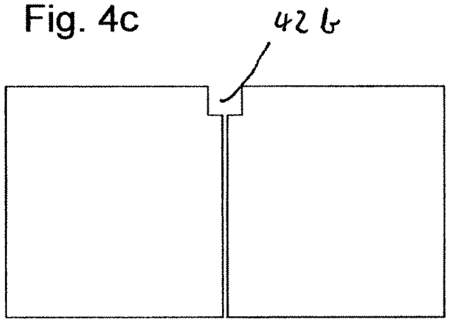
Figure 4D:
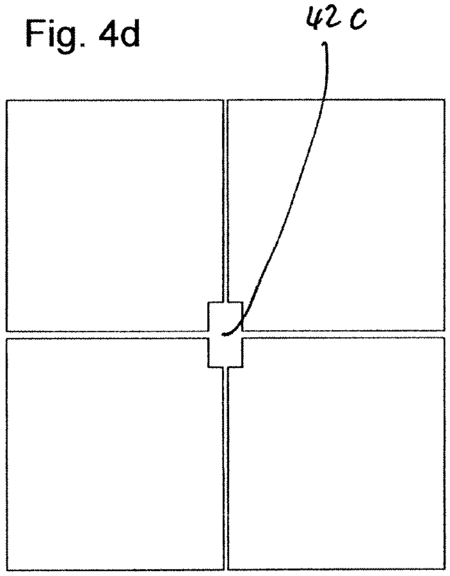

FIGS. 4*b*, 4*c* and 4*d* show the top view on two or four tempering devices, arranged side by side, for being arranged in a laboratory apparatus according to other embodiments of the present invention.

Figure 5A:
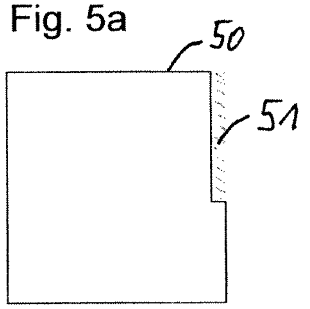

FIG. 5*a* shows the top view on another tempering device, which is shaped to at least partially surround by itself the pressure element, for being arranged in a laboratory apparatus according to another embodiment of the present invention.

Figure 5B:
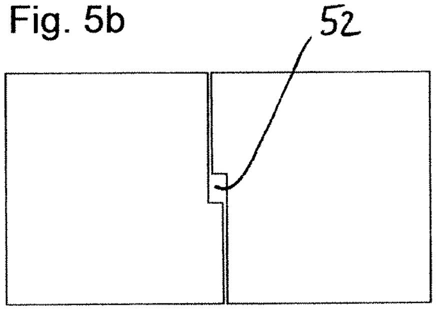

FIG. 5*b* shows the top view on two tempering devices, arranged side by side, for being arranged in a laboratory apparatus according to another embodiment of the present invention.

Figure 6A:
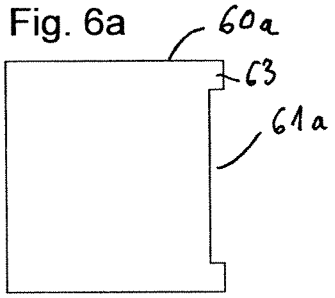
Figure 6C:
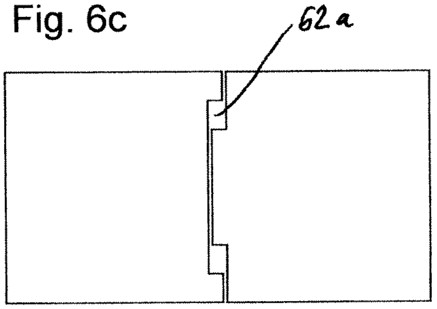
Figure 6B:
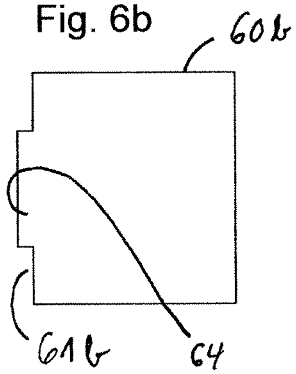

FIGS. 6*a* and 6*b* show the top views on other tempering devices, respectively, which are shaped to at least partially surround by itself, and/or together, the pressure element, for being arranged in a laboratory apparatus according to another embodiment of the present invention.

Figure 6D:
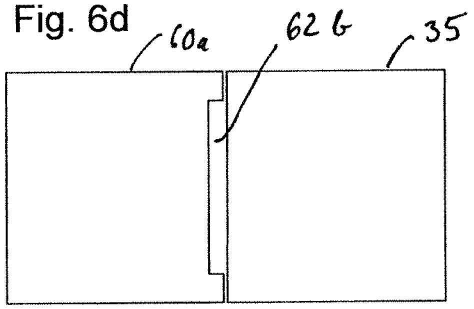
Figure 6E:
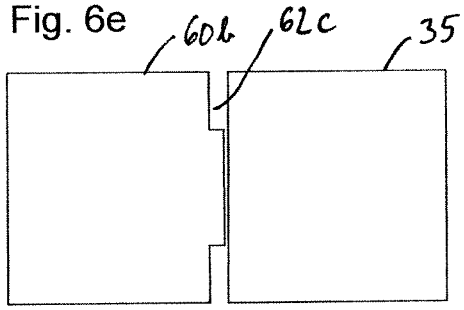

FIGS. 6*c*, 6*d* and 6*e* show the top views on two tempering devices, arranged side by side, for being arranged in a laboratory apparatus according to other embodiments of the present invention.

Figure 7A:
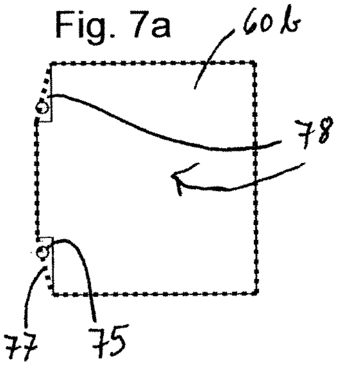

FIG. 7*a* shows in top view the tempering device of FIG. 6*b* and shows two pressure elements (screws), indicating the meaning of the feature “shaped and arranged in said area to at least partially surround by itself the pressure element”.

Figure 7B:
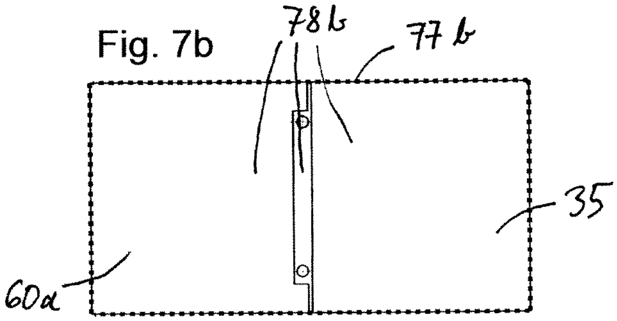
Figure 7C:
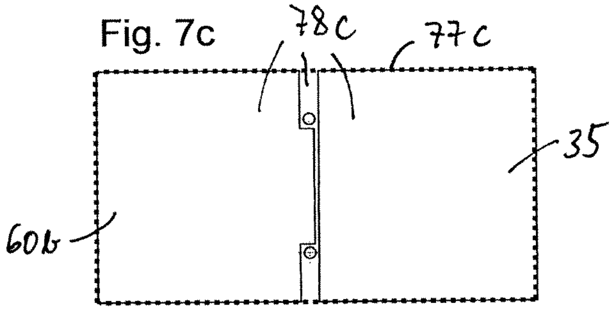

FIGS. 7*b* and 7*c* show in top view the two tempering devices of FIGS. 6*d* and 6*e*, respectively, and show two pressure elements (screws), respectively, indicating the meaning of the feature “shaped and arranged in said area to at least partially surround by itself the pressure element”.

Figure 8A:
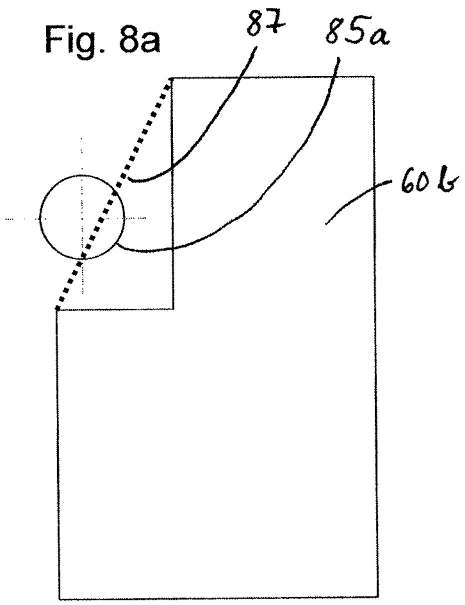
Figure 8B:
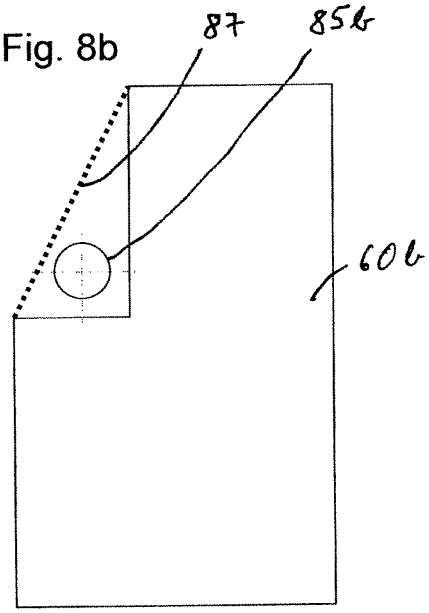

FIGS. 8*a* and 8*b* show in top view a section of FIG. 7*a* and a pressure element (screw), respectively, indicating the meaning of the feature “shaped and arranged in said area to at least partially surround by itself the pressure element”.

Figure 9A:
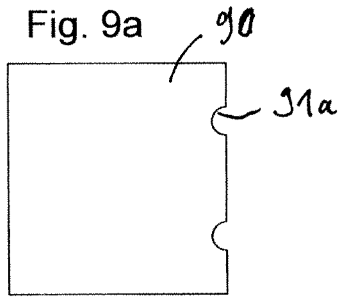

FIG. 9*a* shows the top view on another tempering device, which is shaped to at least partially surround by itself the pressure element, for being arranged in a laboratory apparatus according to another embodiment of the present invention.

Figure 9B:
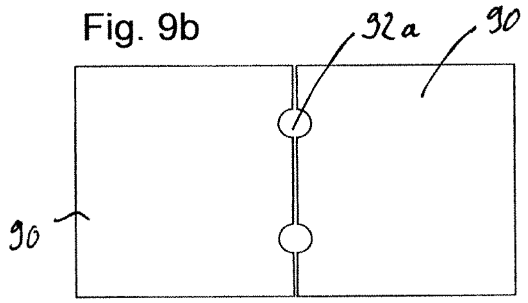
Figure 9C:
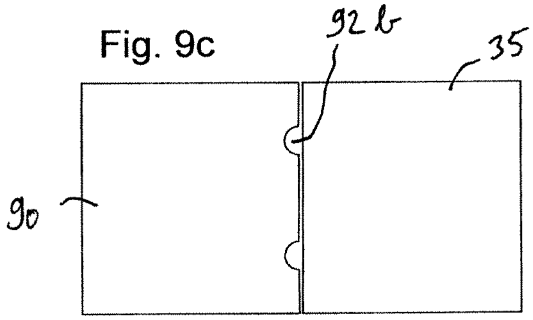
Figure 9D:
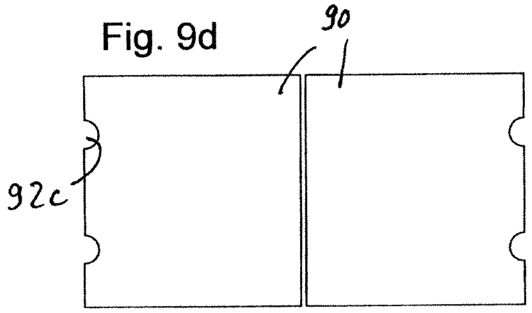

FIGS. 9*b*, 9*c* and 9*d* show the top view on two tempering devices, respectively, arranged side by side, for being arranged in a laboratory apparatus according to another embodiment of the present invention.

Figure 10A:
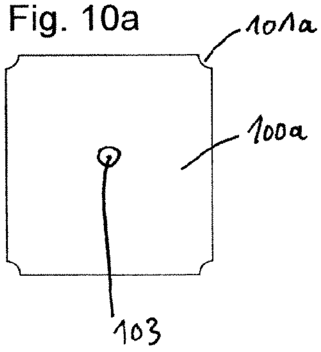

FIG. 10*a* shows the top view on another tempering device, which is shaped to at least partially surround by itself the pressure element, for being arranged in a laboratory apparatus according to another embodiment of the present invention.

Figure 10B:
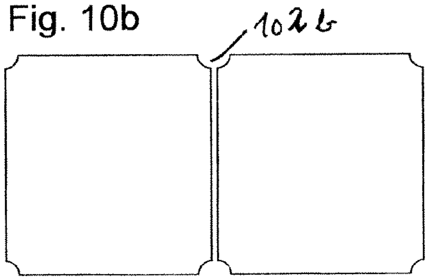
Figure 10C:
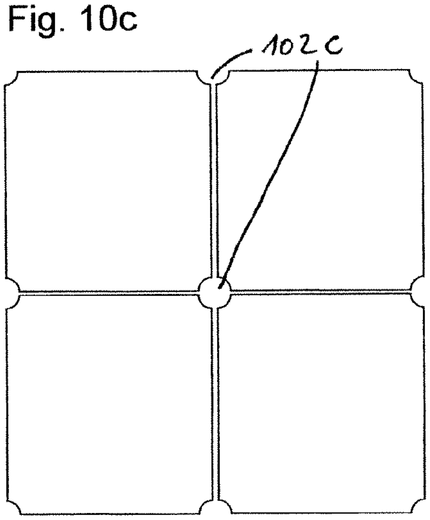

FIGS. 10*b* and 10*c* show the top view on two or four tempering devices of FIG. 10*a*, respectively, arranged side by side, for being arranged in a laboratory apparatus according to another embodiment of the present invention.

Figure 10D:
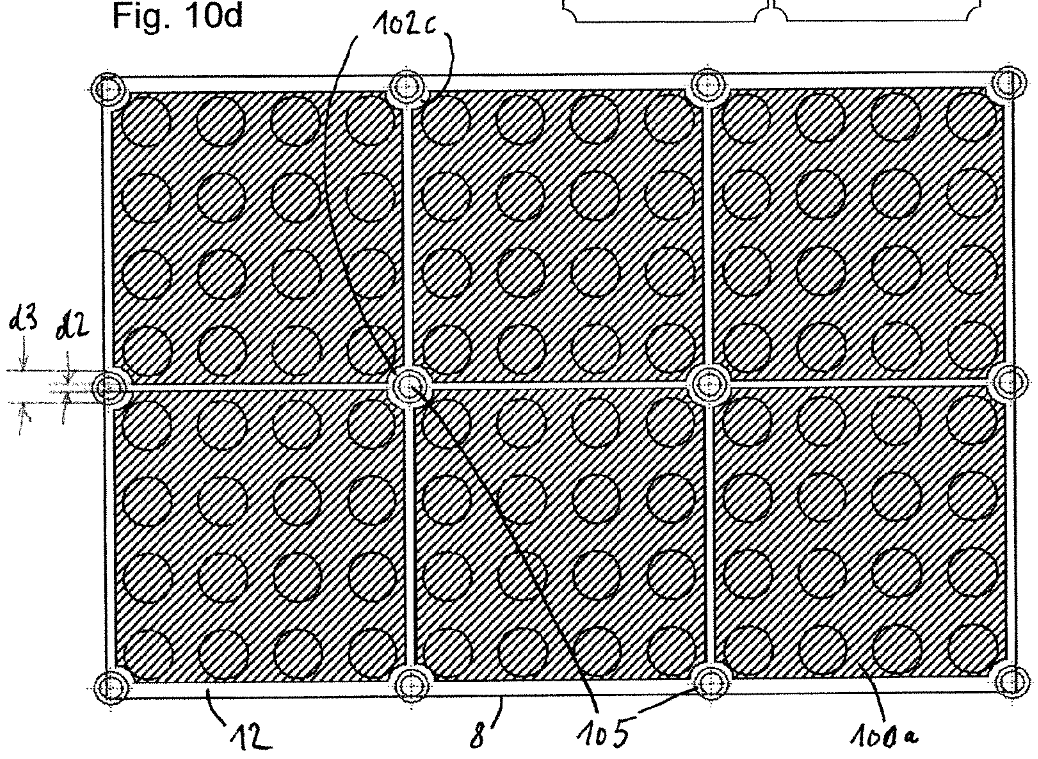

FIG. 10*d* shows the underside of a tempering block of a laboratory according to an embodiment of the present invention, where six tempering devices of FIG. 10*a* are arranged side by side.

Figure 11A:
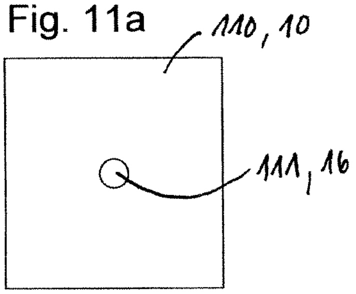

FIG. 11*a* shows the top view on another tempering device, which is shaped to at least partially surround by itself the pressure element, for being arranged in a laboratory apparatus according to another embodiment of the present invention.

Figure 11B:
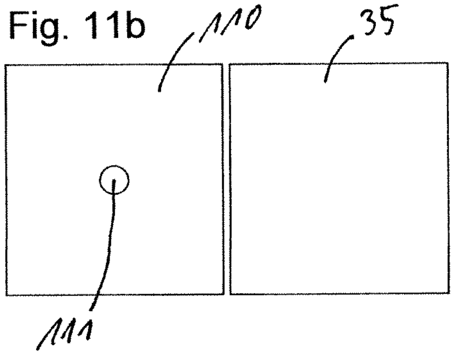
Figure 11C:
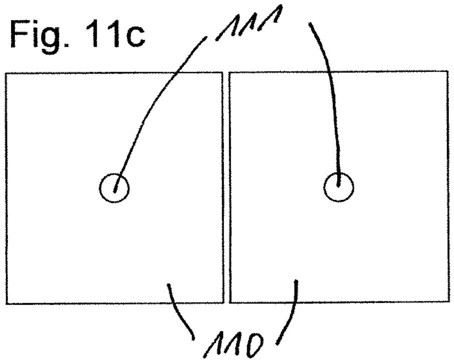

FIGS. 11*b* and 11*c* show the top view on one or two tempering devices of FIG. 11*a*, respectively, arranged side by side, for being arranged in a laboratory apparatus according to another embodiment of the present invention.

Figure 11D:
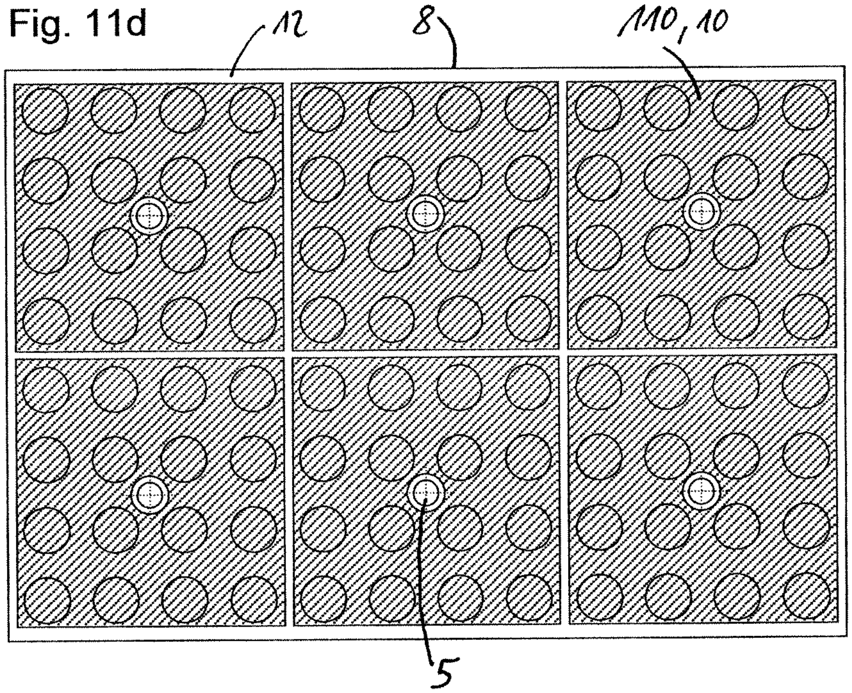
Figure 12A:
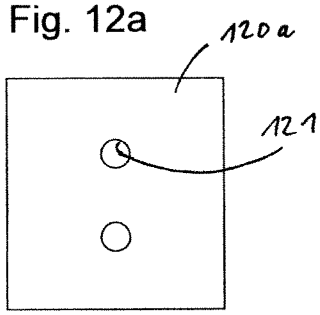
Figure 12B:
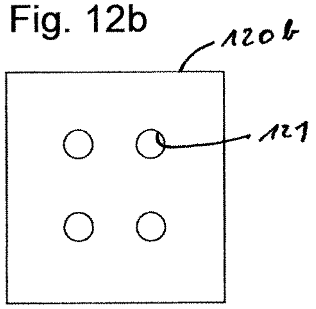
Figure 12C:
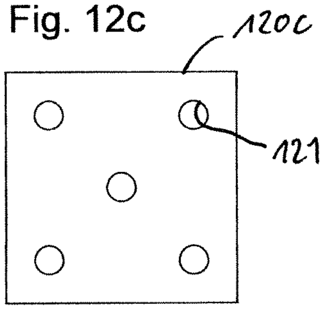
Figure 12D:
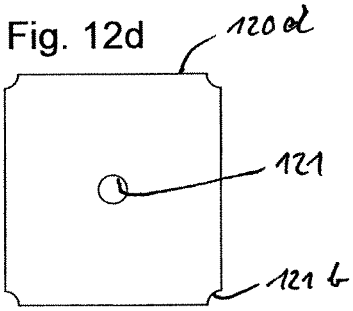

FIG. 11*d* shows the underside of a tempering block of a laboratory according to an embodiment of the present invention, where six tempering devices of FIG. 11*a* are arranged side by side.

FIGS. 12*a*, 12*b*, 12*c* and 12*d* shows the top view on another tempering device, respectively, which is shaped to at least partially surround by itself the pressure element, for being arranged in laboratory apparatus according to other embodiments of the present invention.

Figure 13A:
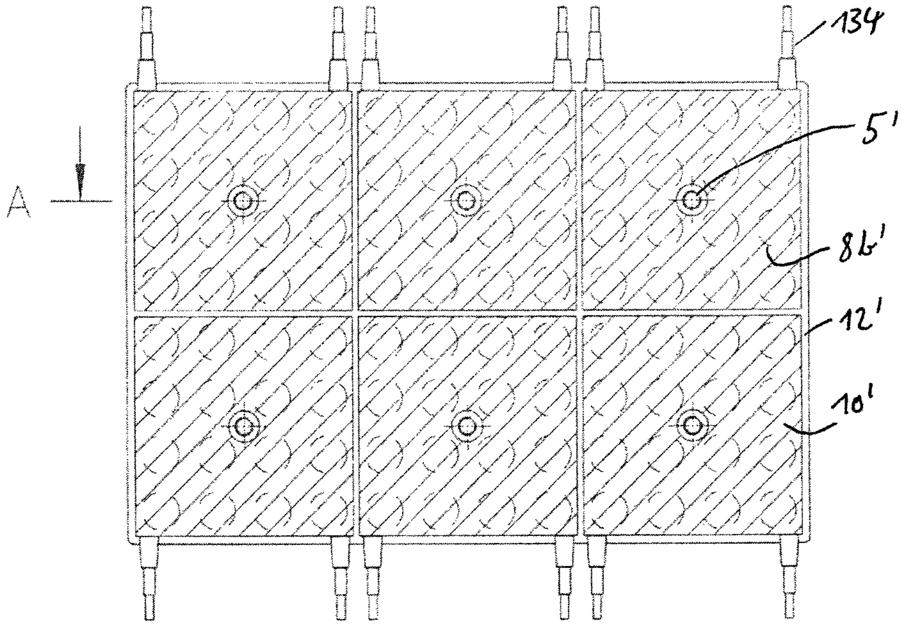

FIG. 13*a* shows in an embodiment similar to FIG. 11*d* the power supply connections of the tempering devices, additionally.

Figure 13B:
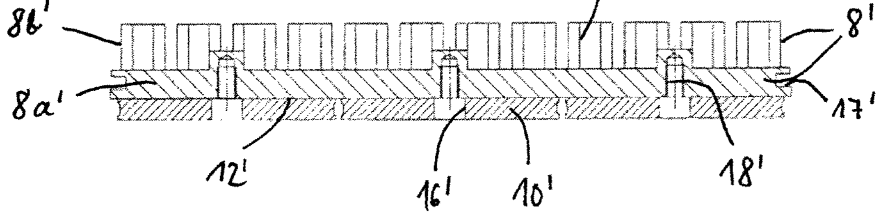

FIG. 13*b* is a cross section of the tempering block of FIG. 13*a*, with tempering devices, along the line ‘A’ in FIG. 13*b*.

Figure 14B:
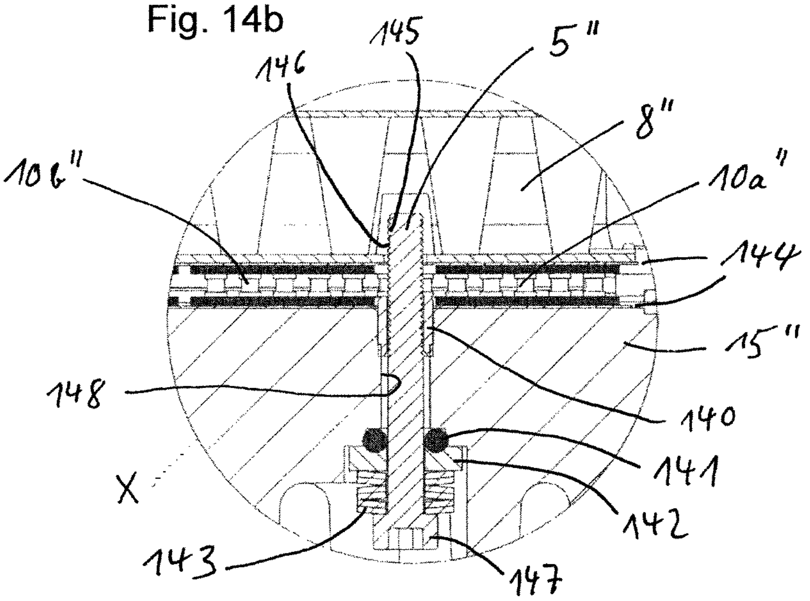
Figure 14A:
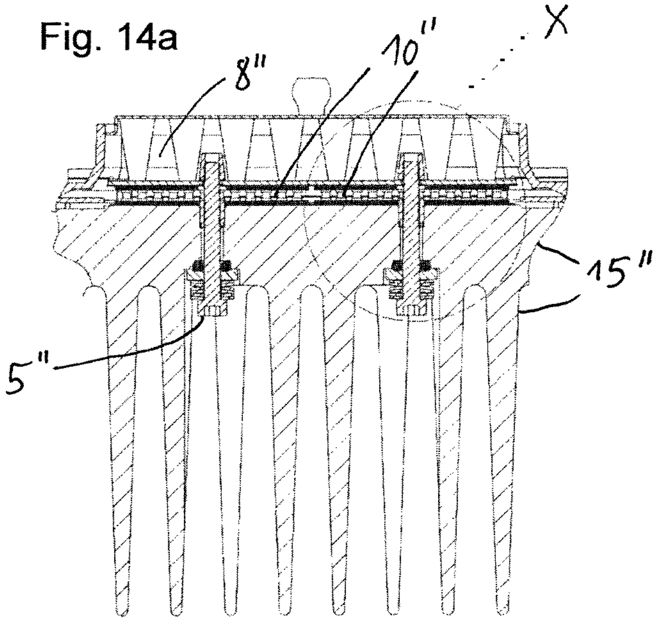

FIG. 14*a* is a more detailed vertical cross section through the arrangement of another tempering block, two tempering devices, pressure elements (screws) and an auxiliary device (heat sink), according to another embodiment of the present invention.

FIG. 14*b* is an enlarged view of the section marked ‘X’ in FIG. 14*a*, showing the position of a pressure element (screw and other components).

FIG. 1 shows a mixed side- and cross sectional view of a laboratory apparatus 1 according to an embodiment of the present invention. The laboratory apparatus 1 has a housing 2, input-/output means 6, a control device 7, an upper side 3, a tempering block 8 with receptacles 11, tempering devices 10, an auxiliary element 15 and a movable cover 4. The exemplary arrangement 100 according to the invention comprises at least the tempering block 8, the tempering devices 10, the auxiliary element 15 and the pressure elements 5.

The laboratory apparatus 1 is adapted to work as a thermocycler for automatically performing a polymerase chain reaction in PCR-samples. The apparatus does this by tempering the PCR samples cyclically to at least two different temperature levels, e.g. a first temperature level for the denaturation of DNA or DNA sections, e.g. between 88° C. and 97° C., and at least a second temperature level for the primer hybridisation and elongation processes, e.g. >55° C., for example, 55° C.-72° C. For this purpose, the apparatus is adapted to store computer program code, or several different program codes, respectively, which controls the PCR by controlling the temperature of the tempering block 8 via the tempering devices 10, which are controlled by a closed loop control, individually or in groups, e.g. pairwise, respectively.

The apparatus 1 is controlled by the electronic control device 7, which also comprises data storage to store the PCR-program code. User interaction with the apparatus is possible via the input-/output means 6. The control device 7 further comprises circuitry for controlling the heat transfer between the tempering devices 10 and the tempering block 8 (heating and cooling, respectively), wherein said circuitry is adapted for a closed loop control of the tempering device. Each control loop comprises two tempering devices, as actuator members of the control loop, and two temperature sensors 19, each temperature sensor assigned to an individual tempering device and measuring the temperature in the section of the tempering block around the sensor. Such an arrangement is preferred to provide the self-diagnosis function to the apparatus, as for example disclosed by PCT/EP2009/005583. Thus, the control device 7 serves to adjust the actual temperature of a monitored section of the tempering block according to a desired target temperature and to shift the target temperature of the tempering block to one or more desired target temperatures, e.g. for cycling the temperatures for performing PCR. The apparatus, or respectively the control device, is adapted to set the block to one single or to multiple target temperatures, e.g. for setting a temperature profile with varying temperatures (gradient) over the length of the block.

The cover 4 can be arranged to cover the upper side 3 and the tempering block 8, as shown, and can be retracted from the closing position to load or unload several, or, respectively, all the receptacles with sample vessels (not shown), which contain a PCR-sample, respectively. Optionally, the cover 4 can be adapted to heat the top portions of the sample vessels, e.g. to avoid the condensation of sample liquid at the inner side of said top portions.

The tempering block 8 is a solid metal block, based on aluminium, and is provided on the upper reception side 13 with 96 receptacles (only eight are shown in the cross section of the arrangement 100), adapted for receiving PCR-vessels or twin.tec PCR plates by EPPENDORF AG in a form closure manner, to allow an optimal transfer of heat from the tempering block to the sample vessels. The contact side 12 of the tempering block is plane, to allow an optimal heat transfer from the tempering devices 10, which also are provided with plane surfaces. The housing 2, the reception side 13, the contact side 12 and the side walls 14 of the tempering block are, in this embodiment, not provided with means, e.g. protrusions or recesses, to press or clamp the tempering devices and the heat sink against the tempering block. This offers the advantage, that the respective sides and adjacent side spaces of the arrangement 100 are free and can be adapted to be used for other purposes, e.g. for mounting skirted PCR plates on the block, which are provided with a stabilizing frame (skirt). This way, the arrangement 100 can be adapted as a thermally independent thermo-unit, which e.g. can be insulated against the other parts of the apparatus, in particular the housing, in particular without providing link means, which may act as thermal bridges. In particular, the pressure device is preferably not using the housing or links to the housing, in order to apply the desired pressure, and is therefore preferably thermally independent on the housing. Preferably, the arrangement is arranged within the apparatus to form a thermo-unit, which is substantially thermally insulated from the apparatus, in particular by providing insulation means on the sides of the arrangement 100 within the apparatus. This way, the temperature uniformity over the tempering block can be further improved.

In the embodiment of FIG. 1, six Peltier elements 10 are provided as tempering devices, which are adapted to set the tempering block to temperatures between −5° C. and 99° C., with a heating rate of e.g. 4° C./sec and a cooling rate of e.g. 3° C./sec for an aluminium block, in particular, 6° C./sec and a cooling rate of e.g. 4.5° C./sec for a silver block, in particular, valid respectively at least between 99° C. and 4° C.

A peltier element 10, in FIG. 1, is shaped according to FIG. 11*a*. It has a basically square silhouette, substantially plane side-, top, and bottom faces, which are substantially perpendicular to each other. In the geometrical center of the tempering device is located a cylindrical recess 16 in the Peltier element, which is arranged perpendicular to the top face of the Peltier element. Said geometrical center is the geometrical center of the plane, which is defined by the silhouette of the tempering device, in relation to the contact side.

Not shown in FIG. 1 are the two connections, which power each respective Peltier element and which are leaving the arrangement 100 from the sides of the Peltier elements. Alternatively, connections can be provided to leave the Peltier element through the wall section of a tempering device, where the same is shaped to at least partially surround by itself the pressure element. For example, a pressure element can be adapted to be assigned to the electrical connection, which powers a Peltier element. A pressure element can be adapted to surround at least partially a power line of the tempering device, e.g. in an insulating manner, or can be adapted to provide a current line, e.g. by forming a current line section, which can be made from a well current conducting material, e.g. copper, or by being arranged and adapted to lead electrical power through the connection body of the pressure element, e.g. the cylinder of a screw.

The Peltier elements 10 are arranged at the contact side of the tempering block according to the arrangement shown in FIG. 11*d*. A tempering device 10 is arranged such that the opening 16 is positioned symmetrically with regard to 16 receptacles of the tempering block. A tempering device 10 is further arranged such that four or eight receptacles, respectively, have the same distance to the opening 16. The tempering device 10 is further arranged such that sixteen receptacles are arranged in opposite to the tempering device, in a way that each vertical tangent of the tempering device, vertical with respect to the horizontal even contact side 12, does not cross the inner volume of a receptacle. This increases the uniformity of the heat transfer to the receptacles and the samples.

A pressure element 5 applies a pressure force via the auxiliary element 15 to the tempering device 10, which basically origins at said center point. Therefore, a substantially uniform pressure is applied to the tempering device, and the heat transfer between the Peltier element and the respective contacted section of the tempering block is improved.

The six Peltier elements are arranged at the contact side 12 such that the distance d2 between vicinal sides of the Peltier elements is uniform. Insulating material can be provided between the Peltier elements, which can be air or another material, e.g. plastics. However, d2 can also be substantially zero.

The pressure element 5 in the embodiment of FIG. 1 comprises an extension bolt 5 with a cylinder with a thread and a head 17, which acts as counter support, if the outer thread of the screw 5 is screwed into a bore of the tempering block with an inner thread, and the counter support 17 abuts around to the opening of the heat sink 15. Pressure is generated upon tightening the screw in a defined way, e.g. by means of a dynamometric key, to apply a controlled pressure, in particular the same pressure on each tempering device. This way, temperature uniformity over the tempering block can be further increased.

In FIGS. 2*a* to 12*d*, different embodiments of tempering devices and/or the respective preferred arrangement according to the invention are shown.

FIG. 2*a* shows the top view on a rectangular- or square-shaped tempering device 20, or, respectively, the silhouette of the same in the top view, which is shaped by providing a rectangular recess 21 to at least partially surround by itself the pressure element, for being arranged in a laboratory apparatus according to an embodiment of the present invention. FIG. 2*b* shows the top view on two tempering devices 20, arranged side by side, for being arranged in a laboratory apparatus according to an embodiment of the present invention. Here, two tempering devices are shaped and arranged to at least partially surround by itself the pressure element and to surround the pressure element substantially completely, i.e. by forming an almost complete ring section 22, which is interrupted only by two small spacer sections 23. The tempering devices 22 are spaced substantially by a distance d2 or, respectively, are spaced by d2, if the ring section 23, formed by the recess 22, is neglected.

FIG. 3*a* shows the top view on another tempering device 30, which is shaped by providing a curved (semi-circle-.shaped) recess 31 to at least partially surround by itself the pressure element, for being arranged in a laboratory apparatus according to another embodiment of the present invention. FIGS. 3*b* and 3*c* show the top view on two tempering devices 32 (FIG. 3*b*) and one tempering device 32 vicinal to a tempering device 35 (FIG. 3*c*), which is not shaped to at least partially, partially or completely surround by itself a pressure element, because the tempering device 35 only has straight side walls. The arrangement in FIG. 3*c* (similar FIGS. 4*b*, 6*d* and the like) can be useful and more inexpensive, if the distribution of pressure elements does not require each tempering device to be shaped to at least partially surround by itself the pressure element, but only a fraction of all tempering devices has to be shaped in the special way, e.g. a fraction of ½, ⅓, ¼, ⅕, ⅙, ⅐, ⅛, ⅑, ⅒ or different. Further, a smaller number of pressure elements can be used, which also applies for the arrangement in FIGS. 2*b*, 3*b* and the like.

FIG. 4*a* shows the top view on another tempering device 40, which is shaped by providing a rectangular recess 41 in a corner to at least partially surround by itself the pressure element, for being arranged in a laboratory apparatus according to another embodiment of the present invention. FIGS. 4*b*, 4*c* and 4*d* show the top view on two or four tempering devices 40, arranged side by side, to form together a rectangular-shaped or square-shaped recess 42*a*, 42*b* or 42*c*, respectively, which is shaped to substantially completely surround together a pressure element.

FIG. 5*a* shows the top view on another tempering device 50, which is shaped by providing a substantially rectangular shaped recess 51 in a side wall, whose length is larger than a side length of the tempering device, to at least partially surround by itself the pressure element. Shown in FIG. 5*b*, in combination with another tempering device 51, a substantially rectangular- or square shaped recess 52 can be provided, the recesses 51 being shaped to substantially completely surround together a pressure element.

FIGS. 6*a* and 6*b* show the top views on other tempering devices 60*a* and 60*b*, respectively, which are shaped by providing a first recess 61*a* and two second recesses 61*b*, in a side wall of a tempering device, respectively, to at least partially surround by itself, and/or together, the pressure element. The recess 61*a* is formed in a side wall of the first tempering device 60*a* such that it is laterally limited by protruding sections 63 of the tempering device 60*a*. The recesses 61*b* of the second tempering device 60*b* are configured preferably such that they form a protruding section 64 in a side wall of the tempering device 64, which preferably can engage recess 61*a* of the first tempering device 60*a*, to preferably form rectangular recess sections 62*a* (FIG. 6*c*), which are respectively shaped to substantially completely surround a pressure element. Alternative recess sections 62*b* and 62*c*, to at least partially surround by itself a pressure element, are shown in FIGS. 6*d* and 6*e*, where a tempering device 60*a* or 60*b* is arranged side by side to a tempering device 35 without special shape, respectively.

FIG. 7*a* shows in top view the tempering device of FIG. 6*b* and shows two pressure elements 75 (screws), indicating with the help of the tempering device 60*b* the preferred general meaning of the feature "shaped and arranged in said area to at least partially surround by itself the pressure element". To "surround" the pressure element partially by a (single) tempering device preferably means that the pressure element 75 is arranged in the enveloping area 78 of said tempering device, which is encompassed by the dotted line 77. Said enveloping area of the tempering device 60*b* is the area, which is enveloped by the virtual line 77, which runs in the plane of a plane contact side, and which envelopes the contact surface, which is the surface of a tempering device 60*b*, which substantially contacts the tempering block on the contacting side. To "surround" the pressure element partially by a (single) tempering device preferably means that the pressure element is arranged in the enveloping area of said tempering device. The virtual line, which envelopes, is in particular defined to span over recesses in the silhouette by straight line sections, as shown in FIGS. 7*a* and 8*a, b*.

Said area 78*b* (or 78*c*) of the contacting side preferably is the area, which is enveloped by a virtual line 77*b* (or 77*c*), which runs in the plane of a plane contact side, and which envelopes the two contact surfaces of the two tempering devices 60*a* and 35 (or 60*b* and 35). This means said area also includes the area between tempering devices 60*a* and 35 (or 60*b* and 35). Reference is mead here to FIGS. 7*b* and 7*c*.

FIGS. 8*a* and 8*b* show in top view a section of FIG. 7*a* and a pressure element 85*a* or 85*b* (screw), respectively, indicating again the meaning of the feature "shaped and arranged in said area to at least partially surround by itself the pressure element". In FIG. 8*a*, the tempering device 60*b* surrounds the pressure element 85*a* at least partially, because the enveloping area (as indicated by the section of the virtual line 87) cuts (and not only touches) the cross section of the pressure element 85*a*, or completely encompasses the cross section of the pressure element 85*b*, respectively.

FIGS. 9*a* and 10*a* are examples for a tempering device 90 and 100*a*, respectively, which is shaped by in particular providing recesses 91*a* (semi-circle-shaped) or in particular 101*a* (quarter-circle-shaped) to surround at least one or a number of pressure elements at least partially by itself. Said number is 2 for the tempering device 90, shown in FIG. 9*a*, and is 4 for the tempering device 100*a*, shown in FIG. 10*a*. For a hexagonal shaped tempering device (not shown), for example, said number can be for example between 1 and 6, preferably 1, 2, 3 or 6. FIGS. 9*b*, 9*c*, 9*d*, 10*b* and 10*c* show exemplary, how the respective tempering devices 90, 35, 100*a* can advantageously be arranged respectively side by side to form together recess sections 92*a*, 92*b*, 92*c*, 102*b*, 102*c*. The recesses 101*a*, in particular, are preferably arranged symmetrical to the geometrical center point 103 of the (preferably square-shaped) tempering device 100*a*, which means that the distance of each portion 101*a*, where the tempering device 100*a* is shaped to at least partially surround a pressure element by itself, to said center point is the same. Thus, a more even pressure distribution can be realized, as shown in FIG. 10*d*.

FIG. 10*d* shows the underside 12 (contact side 12) of a tempering block 8 of a laboratory apparatus 1' according to an embodiment of the present invention, where six tempering devices, which are shaped according to the one of FIG. 10*a* are arranged side by side to provide recess sections 102*c*, which together substantially completely surround a pressure element 105 (e.g. the cylindrical portion of a screw 105). The tempering devices 100*a* are respectively spaced apart in the same distance d2, which is smaller than the width d3 of a pressure element, which is in particular the diameter d3 of the cylindrical portion of a screw 105.

FIG. 11*a* shows the top view on another tempering device 10, 110, which is shaped by providing an opening 16, 111 to surround by itself the pressure element 5, for being arranged in a laboratory apparatus 1 according to an embodiment of the present invention, similar to the one shown in FIG. 1. FIGS. 11 and 11*c* show the top view on one or two tempering devices 110 of FIG. 11*a*, respectively, arranged side by side, for being arranged in a laboratory apparatus according to another embodiment of the present invention.

FIGS. 12*a*, 12*b*, 12*c* and 12*d* shows the top view on other tempering devices 120*a*, 120*b*, 120*c*, 120*d*, respectively, which are respectively shaped by providing one or more (in particular four or five) openings 121 and/or one or more recesses 121*b* to at least partially surround by itself the pressure element, for being arranged in laboratory apparatus according to other embodiments of the present invention.

FIG. 13*a* shows in an embodiment similar to FIG. 11*d* and FIG. 1 the power supply connections 134 of the tempering devices 10', additionally. FIG. 13*b* is a cross section along the line 'A' in FIG. 13*b* of the tempering block of FIG. 13*a* according to a preferred arrangement, with tempering devices 10'. The Peltier elements 10' are arranged to a tempering block 8', similar to the situation in FIG. 1. The block 8' comprises a substantially flat base plate 8*a*', with a plane underside 12', and with receptacle components 8*b*' integrally mounted to the base plate 8*a*' to provide an appropriate heat transfer through the block 8' to the cylindrical-shaped receptacles 11'. Bores 18' with an inner thread are provided at six positions of the contact side 12' of the tempering block 8', the positions distributed symmetrically over the block to achieve a symmetrical pressure- and heat transfer distribution. The sections of the base plate 8*a*', wherein the bores 18' are provided, are about 1.5 times thicker than the base plate at positions between the receptacle components 8*b*'. The openings 16' of the Peltier elements 10' have a larger diameter than the bores 18', to preferably mount a hollow-cylindrical centering sleeve between the screw 5' and the Peltier element 10', whereby the positioning of the Peltier elements is improved while avoiding a direct contact of the outer thread of a screw 5' to the inner side wall of the Peltier element, which otherwise could damage the Peltier element upon screwing or due to long-term-contact. Tempering block 8' provides a recess 17' adapted in the side walls of the base plate 8*a*'. Said recess can be used as additional pressure means, preferably assigned to the pressure device, to press the tempering devices 10' against the contact side 12' especially in the outer border region of the tempering devices 8'. Such additional pressure means can be elastic deformable clamping means, which clamp the auxiliary element (heat sink) against the tempering block, while being small dimensioned to keep the side space adjacent to the side faces of tempering block 8' preferably accessible for other means, e.g. the border section of skirted PCR-plates.

FIG. 14*a* is a more detailed vertical cross section through the arrangement of a tempering block 8", two tempering devices 10", pressure elements 5" (extension screws 5") and an auxiliary device 15" (heat sink 15"), according to another embodiment of the present invention, which is similar to the embodiments in FIGS. 1 and 13*a, b*. FIG. 14*b* is an enlarged view of the section marked 'X' in FIG. 14*a*, showing the position of a pressure element 5" (screw 5" and other components). The arrangement in FIGS. 14*a* and 14*b* can in particular be used for a laboratory apparatus according to the invention or, e.g., as alternative to the arrangement 100 in FIG. 1.

The tempering block 8" with receptacles is made of silver. It comprises an upper silver plate with holes for the reception of sample vessels, a lower silver plate and a plurality of reception compartments made from silver for receiving the sample vessels, the compartments being arranged in an array, provided beneath said holes and mounted, e.g. by galvanization, between said plates. The tempering block 8" is provided with bores 145 with an inner thread to allow the mounting of extension screws 5" with an outer thread 146. Said bores 145 are preferably provided in screw nut members, made preferably from hardened metal, preferably frustum-shaped (see non-hatched area 145 in FIG. 14*b*) for providing a preferably large supporting surface on the lower plate, which improves the uniformity of the pressure distribution. The frustum-shaped nut members are preferably provided with a Teflon™ tape or other insulation means on their circumferential side and on top, to further enhance the thermal uncoupling of the pressure element or the auxiliary element, respectively, from the tempering block. The nut members are not completely fixed to the tempering block but inserted between both plates and pressed to the lower plate by the screw 5". Beyond that, the fastening arrangement (5", 147, 143, 142, 141, 145) of FIGS. 14*a, b* corresponds to the fastening arrangement in FIG. 13*b*.

A left side 10*b*" and a right side 10*a*" of a Peltier element 10" are shown in FIG. 14*a*, which are separated by an opening 16" of the tempering device 10", which is shaped and arranged to completely surround the screw 5". The opening 16" is dimensioned such that a centering sleeve 140 fits in the same by form closure. This way, the Peltier element 10" is centered, but not in direct contact with the screw 5". The heat transfer between the tempering device 10" and the tempering block 8", or the tempering device 10" and the heat sink 15", respectively, is even more improved by using heat conducting pads 144, arranged between the tempering device 10" and the tempering block 8", or the tempering device 10" and the heat sink 15", respectively.

The application of a sufficient uniform pressure is achieved by the pressure element (5", 140, 141, 142, 143), which comprises a ceramic disk ring 142, which serves as substantially non-derformable support for the disk spring(s) 143 and as a heat transfer barrier for thermally uncoupling of the tempering block and the heat sink, which otherwise may be coupled via the screw 5, 5' or 5". Also, the screw 5" is arranged in distance to the heat sink 15" by help of centering sleeve 140. Spring means 143 are used to transfer the pressure force from the head 147 of the screw 5", which serves as counter support, to the heat sink 15". Using such spring means 143 and a disk ring 142 allows to more precisely apply a defined pressure than in the case of no spring means 143, as for example in FIG. 1, because the pressure increases more slowly while the screw is slowly displaced towards the tempering block upon tightening. Using a sealing means like the O-ring 141, made from rubber or a material based on Polytetrafluorethylen (e.g. Teflon®), allows to seal the hollow compartment, which is confined by the cylindrical-shaped opening 148 of the auxiliary device 15", the opening 16" and the bore 145. Therefore, the pressure element and the inner sides of the Peltier elements are sealed against the contamination by undesired matter, as for example water vapour and other corroding gasses or liquids, which otherwise may induce a certain long-term damage of the Peltier elements or the pressure element and compromise the long-term reliability of the pressure device and its important function, to provide a uniform heat transfer from the tempering elements to the tempering block.

The invention claimed is:

1. Laboratory apparatus (1), in particular for performing a polymerase chain reaction (PCR) in a plurality of PCR-samples, which comprises an arrangement (100) for tempering samples, the arrangement comprising a tempering block (8; 8'; 8") for the tempering of samples, the tempering block comprising a reception side (13), which provides receptacles (11; 11') for receiving sample vessels, and a contact side (12; 12') for the contact of at least one tempering device, at least one tempering device (10; 10'; 10"; 20; 30; 35; 40; 50; 60*a*; 60*b*; 90; 100*a*; 110; 120*a*; 120*b*; 120*c*; 120*d*), arranged in an area of said contact side, a pressure device, which comprises a pressure element (5; 5'; 5") and an auxiliary element (15; 15"), said at least one tempering device being arranged between said auxiliary element and the tempering block, the pressure element being linked to said auxiliary element and to the tempering block, and being arranged to press said at least one tempering device against the tempering block by pressing said auxiliary element against said at least one tempering device, characterized in that at least one single tempering device is shaped and arranged in said area to at least partially surround by itself said pressure element, wherein said pressure element is arranged to cross the enveloping area, which is the area, which is enveloped by a virtual line (77, 87), which runs in the plane of the even contact side, and which envelops the contact surface, which is the surface of the single tempering device, which contacts the tempering block on the contacting side.

2. Laboratory apparatus according to claim 1, wherein at least two tempering devices are provided, arranged side by side in an area of said contact side.

3. Laboratory apparatus according to claim 2, wherein said at least two tempering devices and said pressure element are respectively configured and arranged such that a minimal distance d2 of said at least two tempering devices is provided.

4. Laboratory apparatus according to claim 3, wherein d2 is smaller than the width of said pressure element.

5. Laboratory apparatus according to claim 3, wherein d2 is smaller than the diameter of said pressure element at a position of said pressure element, which has a minimal distance from said at least one tempering device.

6. Laboratory apparatus according to claim 1, wherein the arrangement is arranged within the apparatus to form a thermo-unit, which is thermally insulated from the apparatus.

7. Laboratory apparatus according to claim 1, wherein the tempering device is shaped to at least partially surround said pressure element by comprising at least one opening.

8. Laboratory apparatus according to claim 7, wherein the opening is a recess in the side wall of the tempering device.

9. Laboratory apparatus according to claim 1, wherein said at least one tempering device is arranged to, respectively preferably, partially or completely surround by itself said pressure element.

10. Laboratory apparatus according to claim 1, wherein said pressure element and at least one tempering device are arranged such that the pressure element crosses the geometrical center point (103) of said tempering device (100*a*).

11. Laboratory apparatus according to claim 1, wherein a plurality of pressure elements are provided, which are respectively at least partially or completely surrounded by a single tempering device.

12. Laboratory apparatus according to claim 11, wherein at least two pressure elements are arranged in the same distance to the geometrical center point (103) of said tempering device (100*a*).

13. Laboratory apparatus according to claim 1, wherein said auxiliary element (15) is adapted to serve as a heat sink (15) for the heat, which is generated by said at least one tempering device.

14. Laboratory apparatus according to claim 1, wherein said at least one tempering device is a Peltier element.

15. Laboratory apparatus according to claim 1 which is adapted to be a Thermocycler for automatically performing a PCR in a PCR-sample.

16. Method for tempering samples by means of a laboratory apparatus, in particular according to one of the previous claims, Laboratory apparatus, in particular for performing a polymerase chain reaction (PCR) in a plurality of PCR-sample, which comprises an arrangement for tempering, the arrangement comprising a tempering block for the tempering of samples, the tempering block comprising a reception side, which provides receptacles for receiving sample vessels, and a contact side for the contact of tempering devices, at least one tempering device, arranged at an area of said contact side, a pressure device, which comprises a pressure element and an auxiliary element, said at least one tempering device being arranged between said auxiliary element and the tempering block, the pressure element being linked to said auxiliary element and to the tempering block, and being arranged to press said at least one tempering device against the tempering block by pressing said auxiliary element against said at least one tempering device, wherein tempering is performed by means of at least one single tempering device, which is shaped and arranged in said area to at least partially surround said pressure element, wherein said pressure element is arranged to cross the enveloping area, which is the area, which is enveloped by a virtual line (77, 87), which runs in the plane of the even contact side, and which envelops the contact surface, which is the surface of the single tempering device, which contacts the tempering block on the contacting side.

* * * * *